United States Patent

Bonnell et al.

Patent Number: 5,997,472
Date of Patent: Dec. 7, 1999

[54] ENDODIAGNOSTIC METHOD USING DIFFERENTIAL THERMAL RELAXATION AND IR IMAGING

[75] Inventors: Leonard J. Bonnell, Huntingdon Valley, Pa.; Dennis C. Leiner, Jaffrey, N.H.; Thomas Brukilacchio, Reading, Mass.

[73] Assignee: Vipera Systems, Inc., Huntingdon Valley, Pa.

[21] Appl. No.: 08/880,686

[22] Filed: Jun. 23, 1997

Related U.S. Application Data

[62] Division of application No. 08/421,949, Apr. 14, 1995, Pat. No. 5,711,755.

[51] Int. Cl.⁶ ....................................................... A61B 6/00
[52] U.S. Cl. ............................................. 600/109; 600/473
[58] Field of Search ..................................... 600/473, 474, 600/475, 109, 160

[56] References Cited

U.S. PATENT DOCUMENTS

| | | |
|---|---|---|
| 4,122,853 | 10/1978 | Smith . |
| 4,366,381 | 12/1982 | Fischer et al. ........................... 600/474 |
| 4,418,689 | 12/1983 | Kanazawa . |
| 4,783,593 | 11/1988 | Noble . |
| 4,786,813 | 11/1988 | Svanberg et al. . |
| 4,817,622 | 4/1989 | Pennypacker et al. ................. 600/473 |
| 4,820,923 | 4/1989 | Wellman . |
| 4,872,458 | 10/1989 | Kanehira et al. . |
| 4,905,082 | 2/1990 | Nisigaki et al. . |
| 4,945,409 | 7/1990 | Nakamura . |
| 4,951,133 | 8/1990 | Onada . |
| 4,995,398 | 2/1991 | Turnidge . |
| 5,021,657 | 6/1991 | Kettlewell et al. . |
| 5,056,525 | 10/1991 | Hafezi ..................................... 600/474 |
| 5,133,605 | 7/1992 | Nakamura . |
| 5,147,354 | 9/1992 | Botacoff et al. . |
| 5,177,605 | 1/1993 | Takahashi et al. . |
| 5,305,759 | 4/1994 | Kaneko et al. . |
| 5,444,250 | 8/1995 | Hanke . |
| 5,445,157 | 8/1995 | Adachi et al. .......................... 600/474 |
| 5,596,992 | 1/1997 | Haaland et al. ........................ 600/473 |
| 5,790,586 | 8/1998 | Hilton, Jr. et al. ..................... 600/474 |

FOREIGN PATENT DOCUMENTS

| | | |
|---|---|---|
| 0174713 | 7/1987 | Japan . |
| 0174715 | 7/1987 | Japan . |
| 0174716 | 7/1987 | Japan . |

*Primary Examiner*—John P. Leubecker
*Attorney, Agent, or Firm*—Francis J. Caufield

[57] ABSTRACT

Endodiagnostic methods utilize differential thermal relaxation and IR and visible imaging to differentiate between normal and abnormal interior body structures and tissue. With the use of a separate or integrated visible endoscope, an interior body site to be examined is visualized and then the area of interest is flooded with a cooling liquid. Upon contact with the area of interest, an immediate cooling of the flush site takes place, thus providing a temperature differential of approximately 25 degrees Fahrenheit of the cooled site compared to surrounding body-temperature tissue. As the area warms back to the surrounding tissue temperature, abnormal areas can be visualized because their temperature warms at a different rate compared to normal structure or tissue. As time progresses the contrast between normal and abnormal reaches a maximum and then declines as both relax back to body temperature. During the relaxation period infrared emissions within the range including 2 to 14 micrometers are visualized in the form of encoded images to permit differential analysis. This is done via endoscopic apparatus having separate or integrated IR and visible channels. The IR channel preferably comprises a refractive objective lens for forming a real image of interior structure of interest, a relay system consisting solely of refracting elements for transferring the real image to an intermediate image plane conjugate to the objective image plane, and a refracting coupling lens for forming a final image of the intermediate image in a detector plane for an IR detector sensitive in the range including 2 to 14 micrometers.

5 Claims, 9 Drawing Sheets

ENDODIAGNOSTIC METHOD USING DIFFERENTIAL THERMAL RELAXATION AND IR IMAGING

This application is a division of application Ser. No. 08/421,949 filed Apr. 14, 1995 which application is now U.S. Pat. No. 5,711,755.

BACKGROUND OF THE INVENTION

1. Field of the Invention

This invention relates generally to the field of endoscopic surgery and more particularly to diagnostic systems employing novel endoscopic apparatus and methods operating at and beyond the two (2) micron region of the spectrum.

2. Description of the Prior Art

Endoscopic surgery (ES) continues its rapid evolutionary progress as a minimal access surgical technique that reduces patient trauma while not compromising the operating field. Operations are performed in a closed physiological environment though the use of specialty designed, elongated instruments that are introduced into body cavities via relatively small cannulas (5 to 10 mm or so) and manipulated with visual guidance provided with either direct optical systems or, more recently, video systems. Compared with open surgical procedures, one major advantage of ES flows from the reduction in the severity of parietal wounds even though several cannula are usually used to gain access to the surgical sight. And, there are other advantages including a lessening of postoperative catabolic response, reduction in interior cooling and desiccation due to evaporation, fewer retraction related injuries, fewer adhesions and infections, and shorter hospital stays, along with associated costs.

ES approaches have commonly been used for laparoscopic surgery and are more frequently being adapted to other procedures such as endoluminal, perivisceral, intra-articular, thoracic, and combinations of these.

However, if the benefits of ES are to be more fully realized, diagnostic procedures are needed that will permit rapid in situ evaluation of pathology while the surgical procedures are in progress. Presently, this is not possible without significant time delays and the use of relatively complicated x-ray techniques requiring the injection of contrast dyes.

The negative impact caused by the lack of rapid least-invasive diagnostic procedures can be illustrated by considering one common ES procedure, the laparoscopic cholecystectomy for removal of the gall bladder. As is known, the cystic duct connects the gall bladder to the common bile duct which, in turn, leads to the duodenum. During a laparoscopic cholecystectomy, a diseased gall bladder is excised and removed from the body. In 3–5% of patients with diseased gall bladders, stones are not only present in the gall bladder but are also present in the cystic duct or in the vicinity of the sphincter connecting the cystic duct with the common bile duct. Retained stones present in the sphincter may cause post-operative discomfort to the patient and/or require further surgical intervention.

In the current art, this discomfort may be avoided by performing a cholangiogram during the cholecystectomy. To accomplish this, a fluoroscope is used to visualize any stones present. If a stone is observed from the cholangiogram, a secondary procedure is conducted in which a slit is made through the cystic duct. A flexible endoscope is then passed through this slit to observe the retained stones. A working channel within the flexible endoscope is equipped with a grasping forceps to remove any stones found. The flexible endoscope is of small enough diameter (~2 mm) to allow entrance into the 6 mm diameter cystic duct.

This secondary procedure has the disadvantage that it is very time-consuming and expensive because the cholecystectomy must be interrupted to bring in the fluoroscope and technician. Also, it is not preferred to expose the operating room personnel to the necessary radiation to conduct the fluoroscopy. In fact, in some 80% of the currently administered laparoscopic cholecystectomies, the cholangiogram is omitted, and the patient is at risk of having retained stones in the cystic duct.

Clearly, this and similar procedures require an alternate diagnostic tool for visualizing stones or other abnormalities while ES procedures are being conducted, and it is a primary object to this invention to provide endoscopic apparatus and methods by which such diagnoses may be conducted.

While infrared radiation has been used in the medical field for thermotreatment and other purposes, it appears to have never been used for purposes of diagnosis as advocated hereinafter. Examples of its use from the patent literature are the following:

U.S. Pat. No. 4,122,853 (Smith) discussed a means for treatment using an infrared laser beam. There is no discussion of means for viewing an IR-emitting object;

U.S. Pat. Nos. 4,945,409 (Nakamura) and 4,951,133 (Onoda) discuss miniature cameras which can be used as an endoscope in the UV, Visible, and IR. A filter from a light source rotates to choose the proper wavelength region. The IR region is confined to near IR less than one (1) micron, and there is no discussion regarding self-emission of the body in the mid-IR. Similarly, the Japanese patents are confined to near-IR wavelengths less than 1.2 microns and only to objects that are illuminated by an external source;

U.S. Pat. No. 4,418,689 (Kanazawa) describes an endoscope used with a laser. There is no discussion of an endoscope used in the infrared;

U.S. Pat. No. 4,786813 (Svanberg et.al.) describes a system for detecting fluorescence of an object. The device is limited to wavelengths less than 0.7 microns and only emissions stimulated by external excitation;

U.S. Pat. No. 4,872,458 (Kanehira et.al) describes a thermotherapy device inserted through a conventional visible light flexible or rigid endoscope. In this patent, a heat source generating far-infrared radiation is used for treatment. There is no attempt at visualizing the infrared energy through the endoscope; and U.S. Pat. No. 5,147,354 (Boutacoff et.al.) describes a fiber optic Ho:Yag laser delivery system that can be inserted through an operating channel of a conventional endoscope. Again, there is no attempt to visualize infrared energy.

Consequently, in addition to the primary purpose of the invention, it is an important purpose to provide an endoscope for visualizing interior body structures by providing visible encoded images formed from their infrared emissions.

It is another object of the invention to provide endoscopic systems by which encoded images from infrared emissions from interior body structures can be observed along with images formed from visible light over the same region of interest so that diagnoses may be made via the infrared images and endosurgical procedures performed via the visible images.

It is yet another object of the present invention to provide endoscopic systems in which encoded infrared images and visible light images can be aligned in optical registration for endodiagnostic and endosurgical procedures.

It is still another object of the present invention to provide a means for the use of infrared endodiagnostic procedures for the study of the relationships among infrared images, tissue, and interior body structures to provide a basis for distinguishing normal form abnormal.

It is another object of the present invention to provide an endodiagnostic procedure for detecting the presence of residual stones during and endocholecystectomy.

Other objects of the invention will be apparent and will appear hereinafter in the following detailed description when read in connection with the drawings.

SUMMARY OF THE INVENTION

Endodiagnostic apparatus, systems, and methods are described by which infrared emissions from interior body structures may be visualized in the form of encoded images to permit differentiation between normal and abnormal processes. The encoded infrared images may be used along with other images from the visible spectrum to serve as an adjunct in the performance of endosurgical procedures by permitting contemporaneous endodiagnosis and are particularly efficacious for interoperative diagnosis during laproscopic surgerical procedures such as endoscopic cholecystectomy where the common bile duct requires exploration for the presence of residual stones.

An endoscopic system including an endoscope and associated camera are provided for detecting infrared emissions beyond about 2 microns and converting the detected infrared radiation into visible images in which information about the normalcy of a visualized site is encoded in the form of gray scale or colored images to permit differential diagnosis. When these infrared images are presented aside of images from radiation from the visible spectrum, pathology may be marked for later surgical procedures in the visual channel.

In both the infrared and visual channels of the endodiagnostic system, standard NTSC or PAL video signals are generated for display on video monitors and may be recorded for permanent records.

A preferred method for the visualization of residual stones in the common bile duct during endoscopic cholecystectomy involves thermal perturbation by cooling with sterile saline or Ringer's solution to cause a general depression in the temperature of the site of interest while continuously imaging with the IR endoscope. As the perturbed area proceeds toward thermal equilibrium with the surrounding body tissue temperature, any retained stones can be visualized because the rate at which they approach thermal equilibrium differs from that of the cystic duct itself.

In another embodiment, both the IR diagnostic channel and visible channel are mounted substantially coaxially in a single tube for alignment purposes, which may include compensation for parallax effects.

In addition to its usefulness in the diagnosis of residual stones, the invention is also useful for the detection and identification of abdominal fluid sacs or tumors, highly oxygenated or vascular tumors, blood vessels, and cartilage necrosis in body joints.

DESCRIPTION OF THE DRAWINGS

The structure and operation of the invention, together with other objects and advantages thereof, may best be understood by reading the detailed description in connection with the drawings in which unique reference numerals have been used throughout for each part and wherein.

DETAILED DESCRIPTION

The present invention relates to endodiagnostic apparatus and methods by which infrared emissions from interior body structures may be visualized in the form of encoded images to permit differentiation between normal and abnormal processes. The encoded infrared images may be used along with other images from the visible spectrum to serve as an adjunct in the performance of endosurgical procedures by permitting contemporaneous endodiagnosis and are particularly efficacious for interoperative diagnosis during laproscopic surgerical procedures such as endoscopic cholecystectomy, where the common bile duct requires exploration for the presence of residual stones. The various embodiments of the invention are based on the recognition that significant signal levels may be derived from emissions from interior body structures in the spectral region in the range including 2 to 14 microns, and that these emissions may be selectively altered using thermal relaxation techniques to enhance the thermal contrast between normal and abnormal processes.

Figure 1:
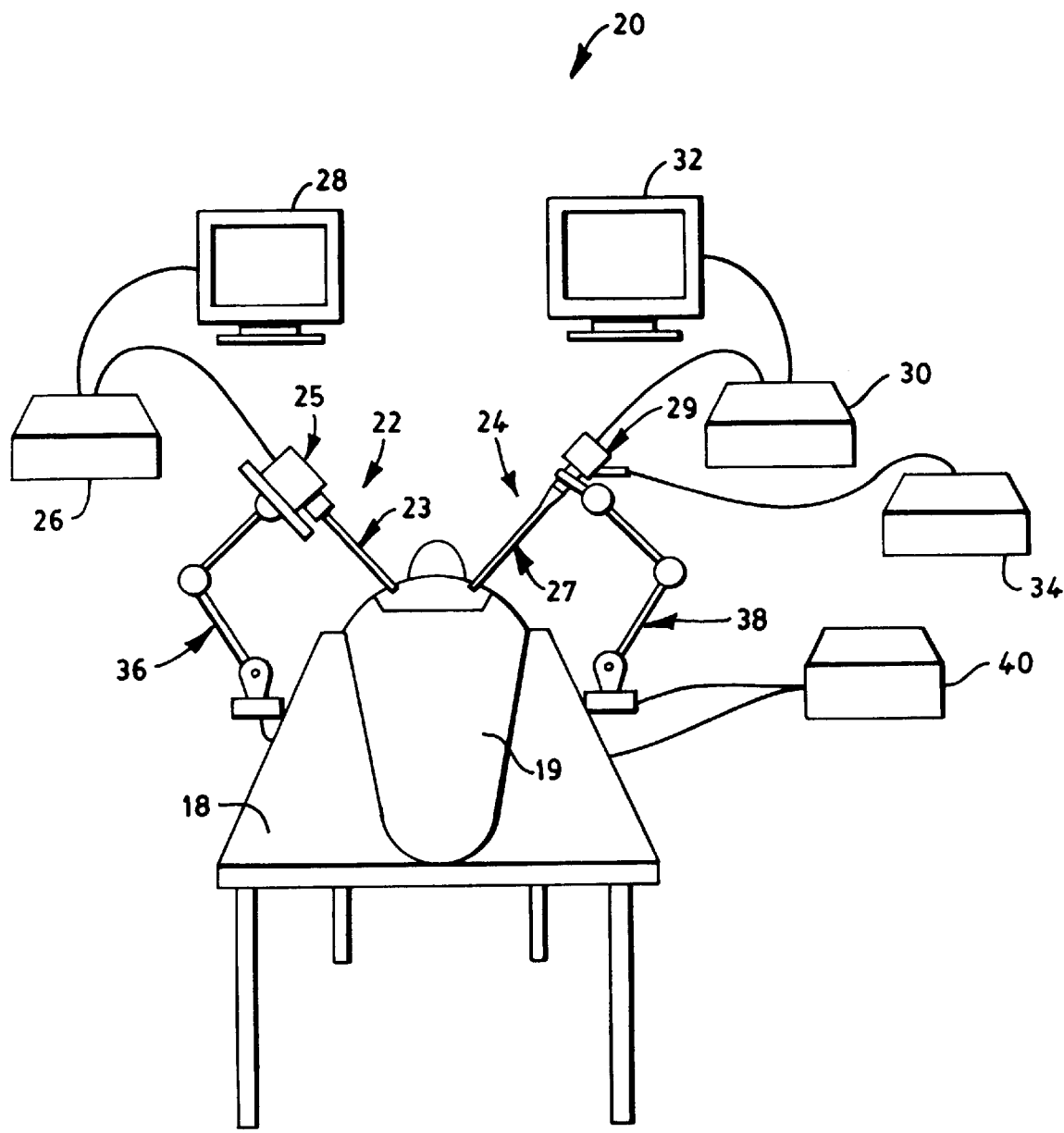
FIG. 1 is a diagrammatic perspective of an inventive diagnostic imaging system of the invention showing infrared and visible radiation endoscopic apparatus for providing encoded images from infrared emissions next to corresponding visible images of substantially the same field of interest.

One preferred embodiment of the invention, designated generally as the system 20, is shown in use FIG. 1 for performing abdominal diagnostic and/or surgical procedures on a patient 19 atop of an operating table 18. System 20 comprises an infrared (IR) endoscopic imager 22 and a visible endoscopic imager 24. IR imager 22 comprises an IR endoscope 23 and an IR video camera 25, and visible imager 24 comprises a visible endoscope 27 and a visible video camera 29.

IR video camera 25 is connected to a video controller 26 for generating standard NTSC or PAL video signals, and the video controller transmits such standard video signals to a video monitor 28 for displaying images carried on the standard video signals.

Visible video camera 29, which may comprise a CCD or vidicon detector or the like, generates a video signal, also in standard video formats, to a visible signal controller 30 which, in turn, transmits it to a video monitor 32 to display images carried via visible video signal. The video signal processing components of the invention may be of well-known conventional design.

Illumination for the visible endoscope 27 is provided by way of a visible light source and controller 34 Preferably, visible light is conducted via fiber optic cables in a manner to be more fully described hereinafter.

IR imager 22 and visible imager 24 are each carried on well-known articulable, pneumatically based and controlled robotic arms 36 and 38, respectively, and both are connected to a pneumatic source and controller 40 to permit the user to position and support the endoscopes as required. Robotic arms 36 and 38 are of the type marketed by Leonard Medical Inc., Huntingdon, Pa. under the trademark "The First Assistant™". Arms 36 and 38 are each provided with three articulating joints that are easily manipulated to permit each endoscopic imager to be moved and locked into place once the desired perspective is achieved or once the imaged fields of interest have been visually aligned in optically registered relationship. For this purpose, arms 36 and 38, are releasably clamped to table 18, and may be moved as needed for the particular imaging task at hand.

In this connection, video monitors 28 and 32 may also be mounted on articulated arms (not shown) of the type that are fastened to a wall so that the monitors may be conveniently moved for optimal viewing conditions. Also, it will be understood that each monitor may display both IR and visible images by way of well-known techniques for splitting screens.

Figure 2:
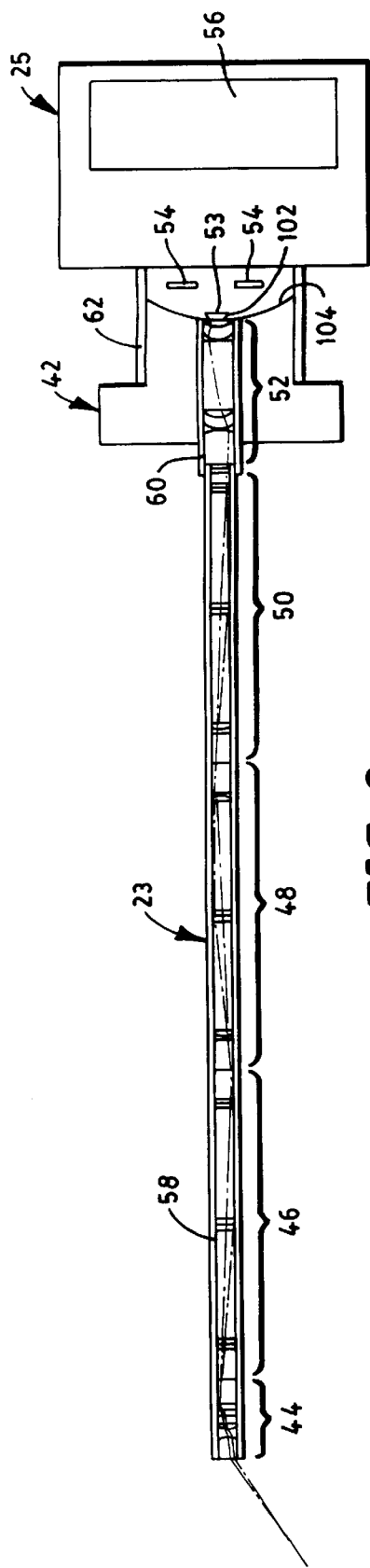
FIG. 2 is a side-elevational view of the infrared endoscope of FIG. 1 with parts shown diagrammatically.

Reference in now made to FIG. 2, which shows various components comprising IR imager 22. As can be seen there, the IR endoscope 23 comprises and objective lens 44 for collecting radiation emitted from an object of interest and forming a real image of it, three identical relay sections, 46, 48, and 50, for transferring the real image to an intermediate image plane located near the endoscope's proximal end, and a coupler lens 52 for forming an image of the intermediate image on an IR detector 53.

IR video camera 25, which includes IR detector 53, is mechanically linked and optically registered with IR endoscope 23 via an adapter 42 that also serves as a warm stop as a consequence of having integrated features for that purpose as will subsequently be explained.

Camera 25 also includes a cold stop 54 for excluding unwanted stray thermal radiation that may otherwise degrade the quality of the IR image by lowering the signal-to-noise ratio of the system.

In this embodiment, all of the elements of the optical train are refractive elements made of Germanium. The elements of objective 44 and relay sections, 46, 48, and 50, are mounted in a well-known manner, in an elongated tube 58 of appropriate length, and the elements comprising the coupler lens are mounted, again in a well-known manner in a sleeve 60 that fits into an appropriately through hole bored in adapter 42. Tube 58 is affixed to sleeve 60, and adapter 42 slides into and is fastened in place in another sleeve 60 that extends forwardly of camera 25 and is adapted to receive adapter 42 and establish its position with respect to IR detector 53 and cold stop 54.

The IR endoscope has an overall track length of 461.73 mm, its semi-field angle is 34°, its working f/# is 5.72, and the diameter of tube 58 is 10 mm so that IR endoscope 23 will fit in standard cannula openings.

Figure 3:
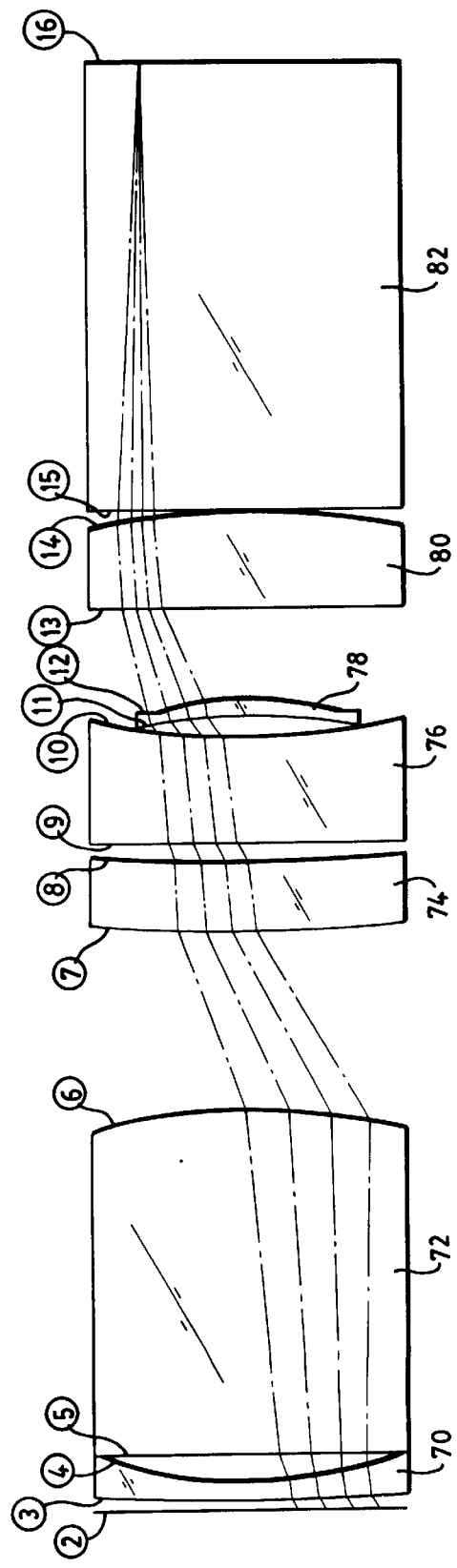
FIG. 3 is an enlarged, side-elevational view of the objective system of the infrared endoscope of FIG. 2.

As best seen in FIG. 3, objective 44 comprises seven elements, a negative meniscus 70, a thick positive double convex element 72, a positive element 74, a negative element 76, a positive meniscus 78, a positive element 80, and a slightly positive rod lens 82. The surfaces themselves are labeled with circled numerals 3 through 16, respectively.

Figure 4:
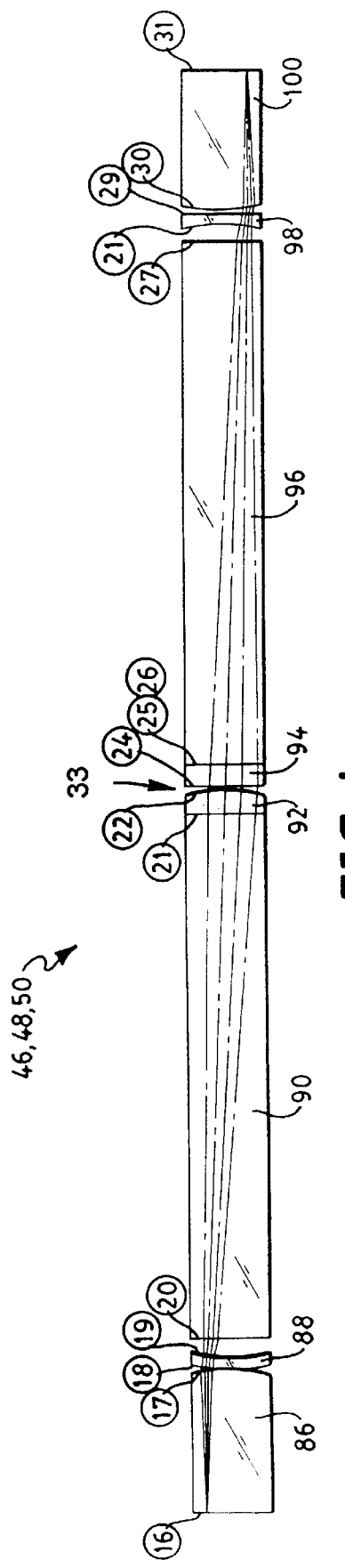
FIG. 4 is an enlarged, side-elevational view of one of the relay systems comprising the infrared endoscope of FIG. 2.

Reference is now made to FIG. 4, which shows a typical relay section of the invention. All of the elements of each relay are identical to those shown in FIG. 4. Three relays are used to achieve the desired length, and an odd number of relays provide an upright image in the intermediate plane, although any number can be used with image orientation handled by proper compensation with camera orientation or other well-known means such as a reversal mirror.

As can be seen in FIG. 4, a typical relay section consists of a piano convex element 86, a meniscus 88, a rod 90, a piano convex element 92, a convex piano element 94, a rod 96, a meniscus 98 and a convex piano element 100. It will be appreciated that the relay sections are symmetrical about the aperture stop of IR endoscope 23, which is indicated with the 33 in FIG. 4. Physically, aperture stop 33 is provided with a real stop made of a low emissivity material, preferably of polished aluminum and preferably coated with gold, and the image of the aperture stop is the real entrance aperture 102 located in the rear curved surface 104 of adapter 42. This is located just before IR detector 53 (See FIG. 2). Aperture stop 33 could also be any other appropriate material coated with gold.

Aperture 102 is located in this manner in adapter 42, which in part serves as a warm stop, at the conjugate of the IR endoscope aperture stop so that it will present the smallest opening for the entry of stray thermal radiation into the IR detection system of camera 25. The various surfaces of the elements of a typical relay are labeled by the circled numerals in FIG. 4.

Figure 5:
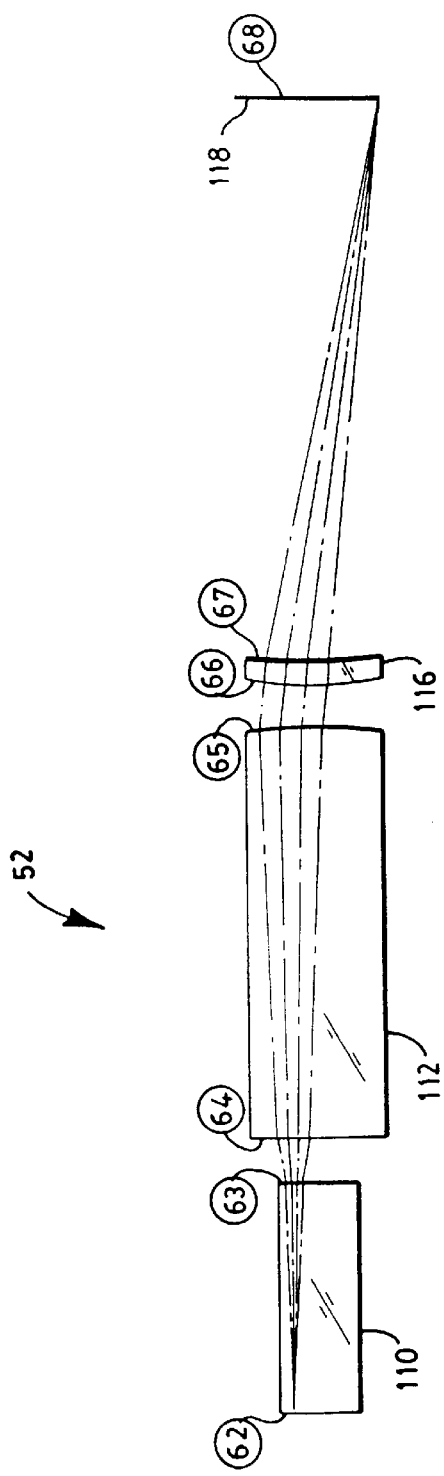
FIG. 5 is an enlarged, side-elevational view of the coupler lens and infrared camera of the infrared endoscope of FIG. 2.

Reference is now made to FIG. 5, which shows the elements of video coupling lens 52. The intermediate image plane is shown at the circled numeral 62. Lens 52 itself comprises negative element 110, positive element 112, thick negative element 114, positive element 116, and finally image 118, which is where IR detector 53 is resident. The following table lists the constructional data for the IR endoscope 23 where dimensions are in mm. In this table, surfaces 31 through 60 simply repeat the constructional data of surfaces 16 through 31 for a typical relay section as shown in FIG. 4.

TABLE I

| Surface | Radius | Thickness | Material | Diameter |
|---|---|---|---|---|
| OBJ | Infinity | 50 | | 72.02901 |
| 1 | Infinity | 0.25 | SAPPHIRE | 7 |
| 2 | Infinity | 0.2 | | 7 |
| 3 | 57.58571 | 0.3987758 | GERMANIUM | 7 |
| 4 | 9.425214 | 0.5789028 | | 7 |
| 5 | 88.87686 | 7.627548 | GERMANIUM | 7 |
| 6 | −15.36183 | 3.957111 | | 7 |
| 7 | 38.17246 | 1.559314 | GERMANIUM | 7 |
| 8 | 47.898 | 0.3581245 | | 7 |
| 9 | 146.2148 | 2.402521 | GERMANIUM | 7 |

TABLE I-continued

| Surface | Radius | Thickness | Material | Diameter |
|---|---|---|---|---|
| 10 | 15.72048 | 0.4595021 | | 7 |
| 11 | -13.73784 | 0.3845466 | GERMANIUM | 7 |
| 12 | -6.854572 | 2.022597 | | 7 |
| 13 | 855.4531 | 2.067545 | GERMANIUM | 7 |
| 14 | -21.05445 | 0.07877675 | | 7 |
| 15 | 6793.881 | 10.0609 | GERMANIUM | 7 |
| 16 | Infinity | 12.2791 | GERMANIUM | 7 |
| 17 | -21.67682 | 0.2 | | 7 |
| 18 | 55.27044 | 1.082979 | GERMANIUM | 7 |
| 19 | 21.05387 | 1.347465 | | 7 |
| 20 | Infinity | 45 | GERMANIUM | 7 |
| 21 | Infinity | 0 | | 7 |
| 22 | Infinity | 2 | GERMANIUM | 7 |
| 23 | | -50.7869 | 0.2 | 7 |
| 24 | 50.7869 | 2 | GERMANIUM | 7 |
| 25 | Infinity | 0 | | 7 |
| 26 | Infinity | 45 | GERMANIUM | 7 |
| 27 | Infinity | 1.347465 | | 7 |
| 28 | -21.05387 | 1.082979 | GERMANIUM | 7 |
| 29 | -55.27044 | 0.2 | | 7 |
| 30 | 21.67682 | 12.2791 | GERMANIUM | 7 |
| 31 | Infinity | 12.2791 | GERMANIUM | 7 |
| 32 | -21.67682 | 0.2 | | 7 |
| 33 | 55.27044 | 1.082979 | GERMANIUM | 7 |
| 34 | 21.05387 | 1.347465 | | 7 |
| 35 | Infinity | 45 | GERMANIUM | 7 |
| 36 | Infinity | 0 | | 7 |
| 37 | Infinity | 2 | GERMANIUM | 7 |
| 38 | -50.7869 | 0.2 | | 7 |
| 39 | 50.7869 | 2 | GERMANIUM | 7 |
| 40 | Infinity | 0 | | 7 |
| 41 | Infinity | 45 | GERMANIUM | 7 |
| 42 | Infinity | 1.347465 | | 7 |
| 43 | -21.05387 | 1.082979 | GERMANIUM | 7 |
| 44 | -55.27044 | 0.2 | | 7 |
| 45 | 21.67682 | 12.2791 | GERMANIUM | 7 |
| 46 | Infinity | 12.2791 | GERMANIUM | 7 |
| 47 | -21.67682 | 0.2 | | 7 |
| 48 | 55.27044 | 1.082979 | GERMANIUM | 7 |
| 49 | 21.05387 | 1.347465 | | 7 |
| 50 | Infinity | 45 | GERMANUM | 7 |
| 51 | Infinity | 0 | | 7 |
| 52 | Infinity | 2 | GERMANIUM | 7 |
| 53 | -50.7869 | 0.2 | | 7 |
| 54 | 50.7869 | 2 | GERMANIUM | 7 |
| 55 | Infinity | 0 | | 7 |
| 56 | Infinity | 45 | GERMANIUM | 7 |
| 57 | Infinity | 1.347465 | | 7 |
| 58 | -21.05387 | 1.082979 | GERMANIUM | 7 |
| 59 | -55.27044 | 0.2 | | 7 |
| 60 | 21.67682 | 5 | GERMANIUM | 7 |
| 61 | 53.0202 | 7.190098 | GERMANIUM | 7 |
| 62 | -1181.617 | 20 | GERMANIUM | 7 |
| 63 | 100 | 4 | | 7 |
| 64 | 220.3955 | 35.78447 | GBRMANIUM | 12 |
| 65 | -65.86031 | 4 | | 12 |
| 66 | 39.62417 | 2 | GERMANIUM | 12 |
| 67 | 59.62065 | 50 | | 12 |
| 68 | Infinity | 0 | 12.84649 | |

Figure 6:
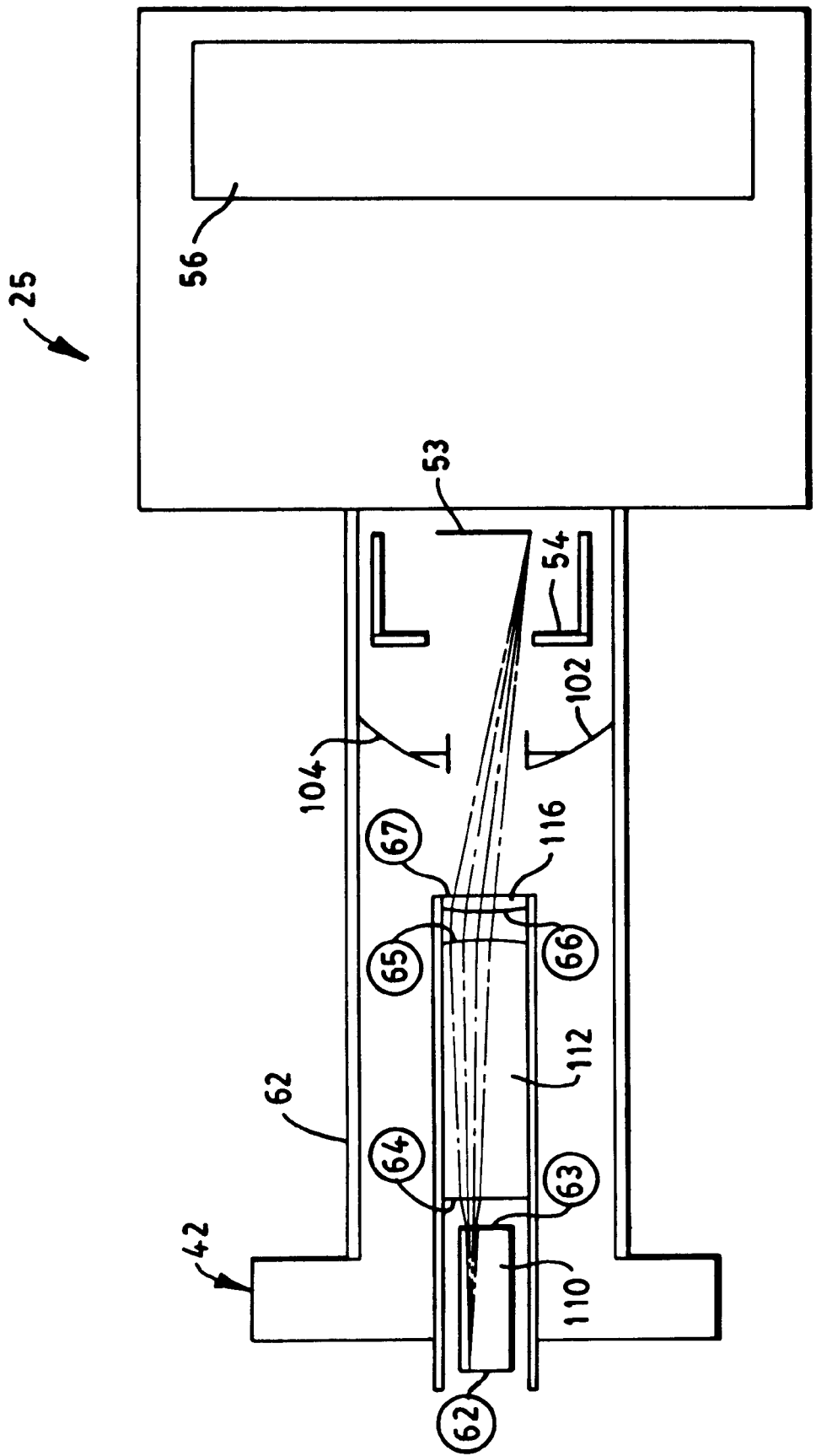
FIG. 6 is an enlarged, side-elevational view of the coupler lens of FIG. 5 shown in combination with the infrared camera of the inventive endoscopic system.

Reference is now made to FIG. 6 which shows in greater detail adapter 42 with its integral warm stop features along with detector 53 and IR video camera 25. As mentioned previously, real (physical) aperture 102 is physically positioned at the image of the aperture stop of IR endoscope 23 and, as such, operates to limit the amount of stray or unwanted thermal radiation that can enter the detection system of camera 25. To further deal with the elimination of stray thermal radiation, camera 25 is provided with cold stop 54 for rejecting stray thermal radiation that might enter the detection system and cause signal degradation. Therefore, the rear surface of adapter 42 is shaped to reflect detector 53 back onto itself so that any stray radiation bouncing around in the detector cavity that finds its way into the field of view of detector 53, as defined in conjunction with aperture 102, is either directly absorbed by cold stop 54 or absorbed by it after one or more reflections as an image back onto cold stop 54. Perferably, detector 53 is placed in a plane that intersects the optical axis at the center of curvature of surface 104.

If a warm stop is not to be used, the field of view and f/# of the camera should be exactly matched with that of the IR endoscope, within tolerances, so that only wanted radiation is collected by the camera, and any stray radiation is directly absorbed by the camera cold stop. Here, the cold stop would be at the aperture stop.

It is to be noted that the above constructional data has been optimized for image quality at 5 microns but, because of the low chromatic dispersion and flat index of refraction profile for Germanium, the image quality over he region from 2 to 14 microns will likewise be acceptable so that the nventive IR endoscope is useable over this extended range.

IR video camera 56 is to be as light weight as possible, and for this purpose is provided with only a preamplifier 56 with most of the signal amplification and control taking place in the distantly located controller 26.

One IR video camera and controller which has been found acceptable is marketed by Amber Corporation, A Raytheon Company, of Goleta, Calif., under the trade name RADI-ANCE 1. This camera has an Indium Antimonide (InSb) detector with 256×256 picture elements and a spectral bandpass of from 3 to 5 microns.

Figure 7:
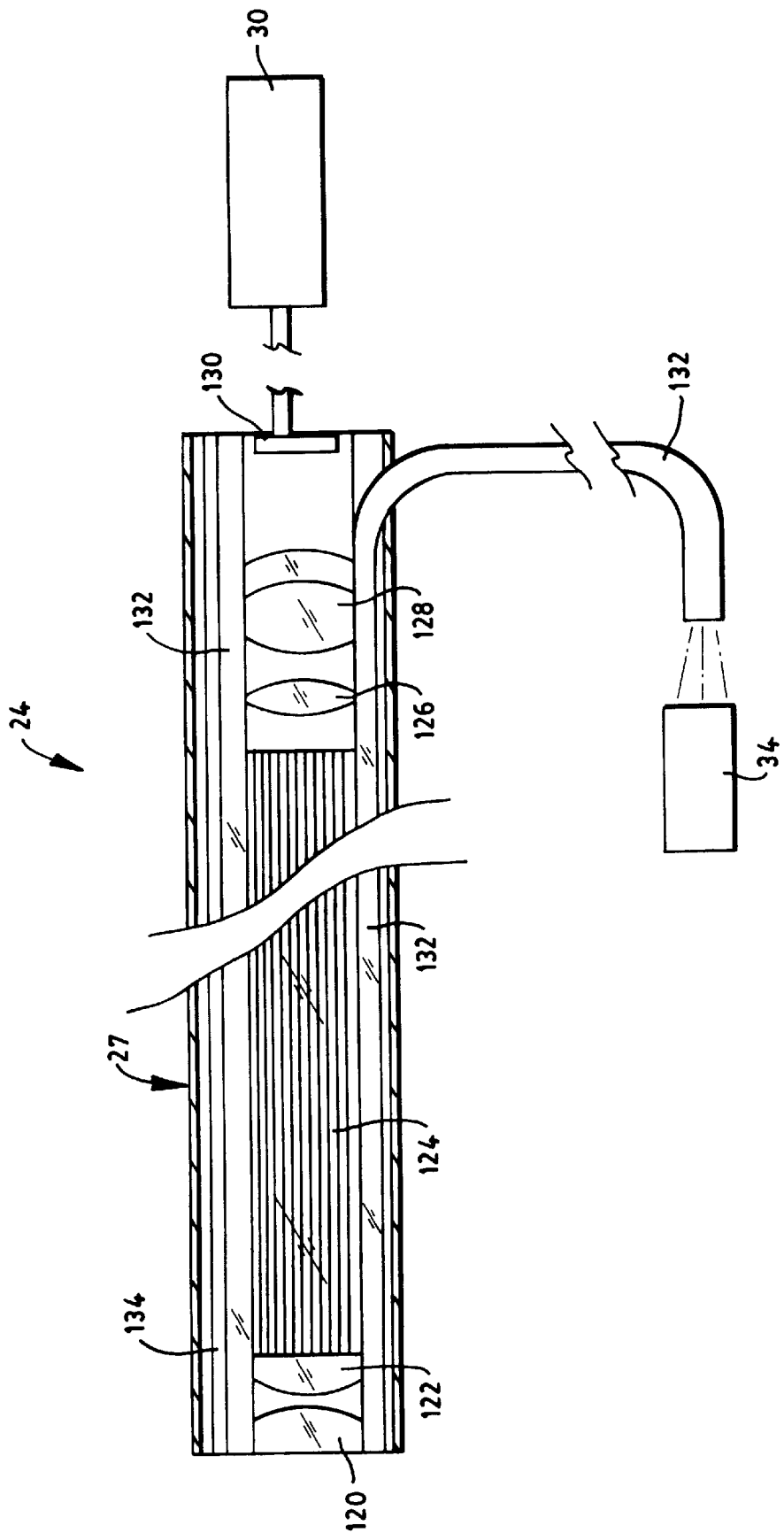
FIG. 7 is an enlarged, diagrammatic, side-elevational view of the visible light endoscope of the system of FIG. 1.

Reference is now made to FIG. 7 which shows the visible endoscope 24. It is seen to comprise an objective which includes two symmetrically arranged piano convex elements, 120 and 122, respectively, which form an image onto or near the end of a coherent fiber optic bundle 124 which transfers the image to the proximal end of the endoscope where it is imaged by a video coupler lens onto a CCD 130. The video coupler lens comprises a singlet 126 followed by a doublet 128. All of the elements of visible endoscope 24 are of well-known design.

Illumination is by way of a fiber bundle 132 which accepts visible light from source and controller 34 and directs it along side the viewing channel toward the distal end for rendering internal body structures visible.

Along side the illumination system, or coaxial with it, is an irrigation channel 134 that may be used to conduct cooling solutions to the internal site being observed for purposes of providing enhanced thermal contrast to those regions in a manner to be described.

Figure 8:
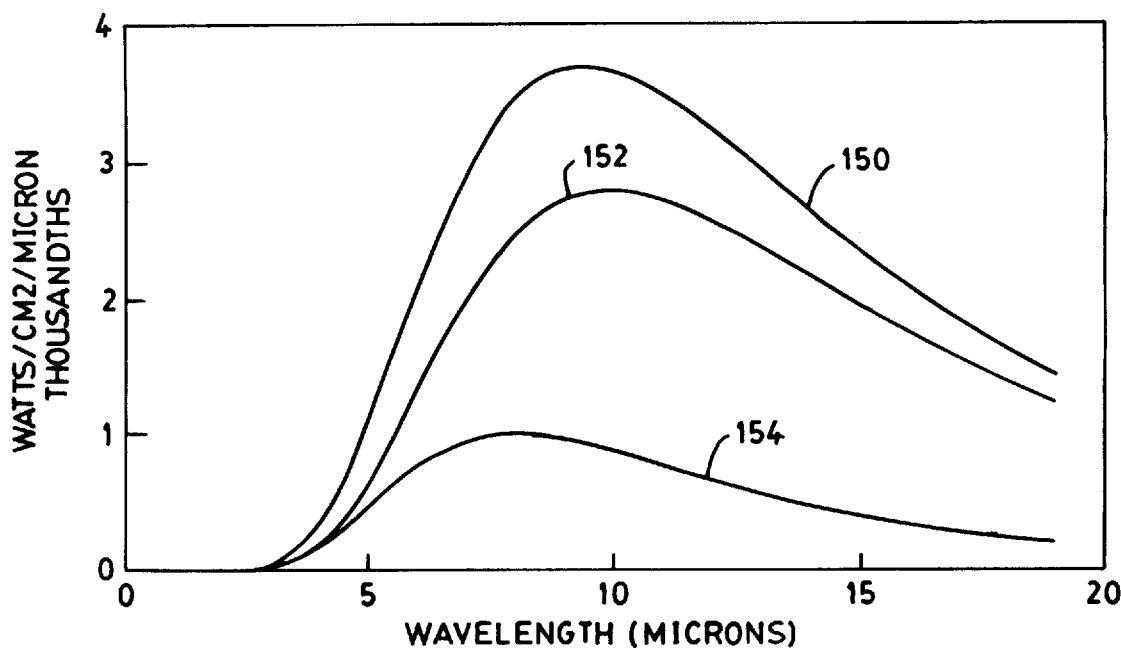
FIG. 8 is a graph showing the infrared radiant emissions from bodies at 98.6° F. and 68° F., along with the difference in IR emissions between them.

The endoscopic system of the invention, thus structured, permits the visualization of otherwise invisible features of internal body structures through the expediency of detecting radiation they emit in the infrared region of the spectrum within the range between 2 and 14 microns. If one looks at FIG. 8, it can be seen that the human body considered as a black body at 98.6° F. (curve 150) has a radiation curve which emits from about 2 to 20 microns with most emissions occurring between about 4 to 15 microns. Consequently, this range of emitted energy has been found sufficient for imaging purposes even at the scale of endoscopes. Moreover, it has been observed that even different body structures at the same temperature will image differently because of differences in their thermal emissivities. Consequently, the IR imager of the present invention is capable of mapping the detected IR emissions as images encoded as differences in either gray scale (monochromatic) or colors (from preselected gamuts) for purposes of providing differential diagnoses which are indicative of normal from abnormal. In addition, it has been found that the addition of cooling solutions to a site of interest will suppress the temperature of that site at least temporarily so that its emissions may look somewhat like curve 152 in FIG. 8, which is for a black body at 68° F., or room temperature. As a site temporarily cooled to room temperature gradually warms up, i.e., approaches thermal equilibrium with its surroundings, here body temperature, it will do so but at different rates corresponding to the thermal properties of the different structures of which it is composed. Therefore, different amounts of thermal energy will be emitted and can be detected to form images. This phenomenon can be exploited since there will typically be a differential heat emission given off by a region that has been temporarily cooled as evidenced by curve 154 in FIG. 8, which shows the difference in thermal energy between curves 150 and 152.

In one particularly important circumstance, the foregoing observations may be beneficially practiced to solve a significant problem that occurs frequently in connection with the removal of gall bladders. As is well-known, the cystic duct connects the gall bladder to the common bile duct which in turn leads to the duodenum. During a laparoscopic cholecystectomy, a diseased gall bladder is excised and removed from the body. In 3–5% of patients with diseased gall bladders, stones are not only present in the gall bladder but are also present in the cystic duct, or in the vicinity of the sphincter connecting the cystic duct with the common bile duct. Retained stones present in this sphincter may cause post-operative discomfort to the patient or require follow-on surgical intervention. In the current art, to avoid this discomfort, a cholangiogram is conducted during the cholecystectomy. The cholangiogram involves the use of a fluoroscope to visualize any stones present. If a stone is observed from the cholangiogram, a secondary procedure is conducted in which a slit is made through the cystic duct. A flexible endoscope is then passed through this slit to observe the retained stones. A working channel within the flexible endoscope is equipped with a grasping forceps to remove any stones found. The flexible endoscope is of small enough diameter (~2 mm) to allow entrance into the 6 mm diameter cystic duct.

This secondary procedure has the disadvantage that it is very time-consuming and expensive to interrupt the cholecystectomy to bring in the fluoroscope and technician. Also, it is not preferred to expose the operating room personnel to the radiation necessary for conducting the fluoroscopy. In fact, in some 80% of the currently administered laparoscopic cholecystectomies, the cholangiogram is omitted and the patient is at risk of having retained stones in the cystic duct and associated complications.

In the method of the present invention, diagnosing retained stones in the cystic duct is accomplished by using infrared laparoscopy. The usual visual laparoscope may be temporarily replaced by an infrared laparoscope having approximately the same diameter so that it can be positioned through the same cannula as the visual laparoscope or the IR laparoscope may have two optical channels, one to provide an image using scattered visible illumination and one to provide an image using IR self-emitted from the body. In an alternate embodiment, a single optical channel may be used to provide both visible and IR images with the two separately proximally using a beamsplitter. No operating channels are used in the preferred embodiment since it is preferable to obtain greater parallax by using an auxiliary operating channel (not shown).

The optical channel containing the visible light forming optics uses conventional lenses such as those present in commercial instruments made by many companies including Circon/ACMI, Storz, Wolf, and others. The visible light optical channel uses a conventional video sensor also available through the foregoing companies. The optical channel containing the infrared light forming optics uses transparent materials in the infrared portion of the spectrum. The IR light optical channel may use one of two types of infrared video sensor. The first type (Indium Antimonide) has relatively high resolution and is most sensitive at about 5 micrometer. A second type, HgCdTe, has relatively poor resolution but is sensitive in the 8–12 micrometer range which is near the peak black body emission curve corresponding to the human body. Also, and preferably, this method uses two separate endoscopes of the type described hereinabove.

Figure 9:
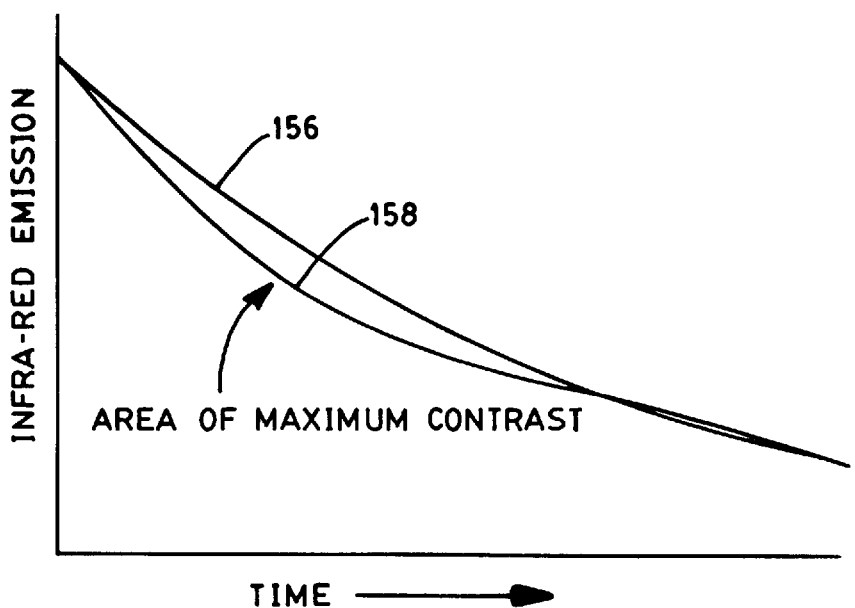
FIG. 9 is a graph illustrating the principle of a differential thermal relaxation method used in practicing one aspect of the invention.

The principal by which the IR laparoscope operates in this instance is by differential thermal relaxation. The area of interest is flushed with room-temperature sterile saline or Ringer's solution. Upon contact with the area of interest (which would include the general area of the cystic duct and sphincter to the common bile duct), an immediate cooling of the flush site will take place. It should be noted that this irrigation may also be by any commonly used sterile fluid dispenser wand made by companies such as C. R. Bard, Johnson & Johnson, and U.S. Surgical Corporation. This room temperature flush provides a temperature differential of approximately 25 degrees Fahrenheit compared to surrounding body-temperature tissue. As the area warms back to the surrounding tissue temperature, any retained stones can be visualized because their temperature warms at a different rate compared to the cystic duct itself. This is illustrated with reference to FIG. 9 where curves 156 and 158 show the different rates, respectively, at which the cystic duct and retained stones return to thermal equilibrium.

As time progresses the contrast between the retained stones and the cystic duct reaches a maximum (see again FIG. 9) and then declines as both the retained stones and cystic duct relax back to body temperature. In addition to the diagnosis of retained stones in the cystic duct, there are other endoscopic procedures that can be improved by a similar infrared technique as described above. These include: diagnosis of fluid sacs or tumors in the abdominal area and diagnosis of highly oxygenated or vascular tumors. In addition, diagnosis of cartilage necrosis in the joints of the body also appears possible.

Figure 10:
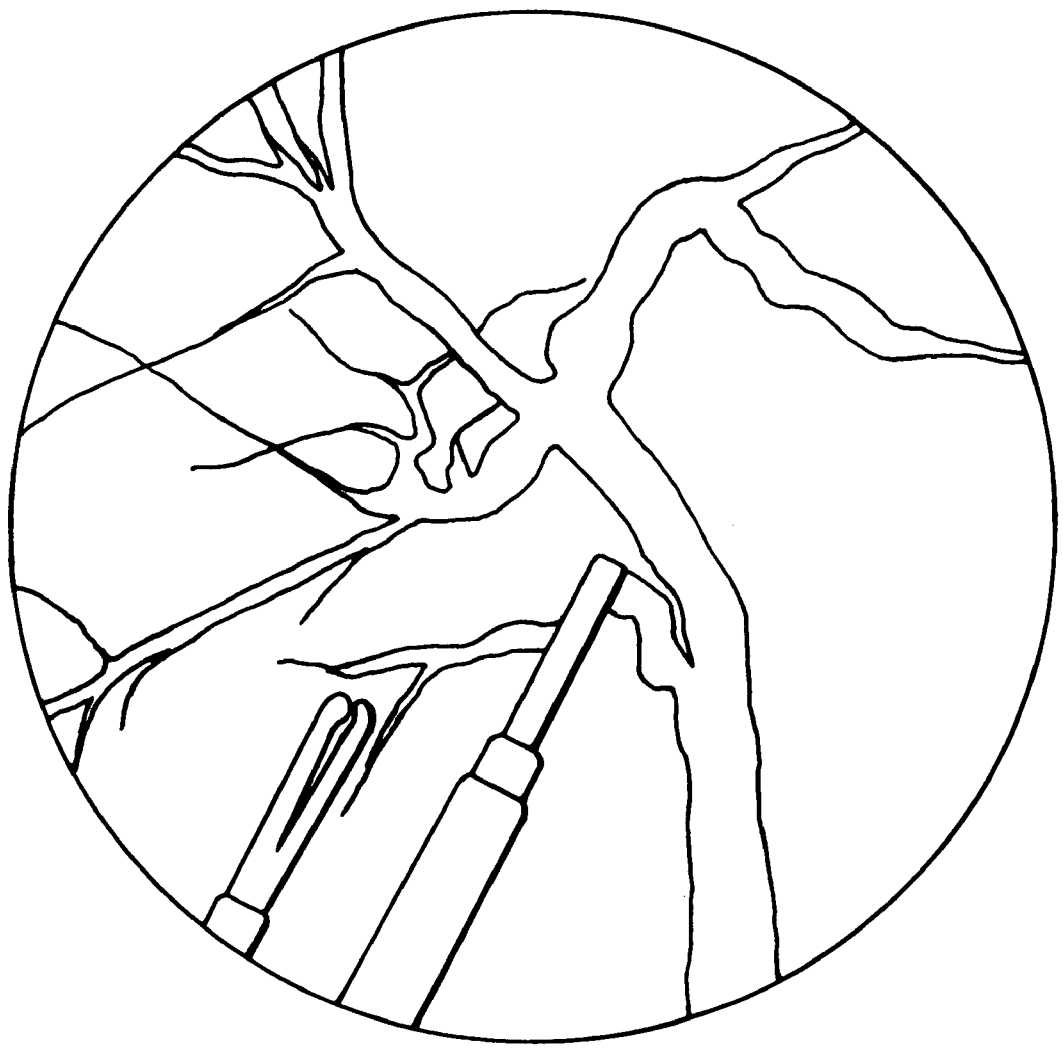
FIG. 10 is a representation of an infrared image of the sort that may be obtained utilizing the invention.

FIG. 10 illustrates how such an infrared image may appear. It shows that instruments, such as clamps may be used to identify or mark abnormal sites in the IR image which then can more easily be operated on via the visible image.

Figure 11:
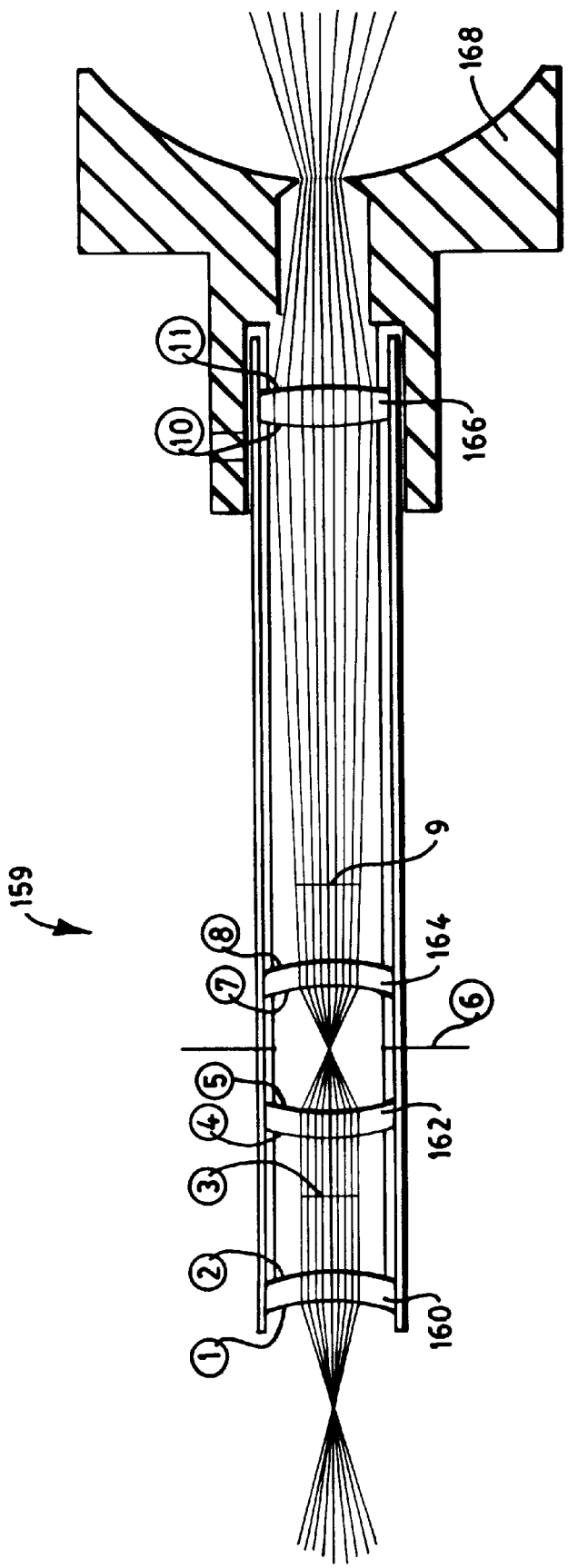
FIG. 11 is an alternate embodiment of infrared endoscope according to the invention.
Figure 13:
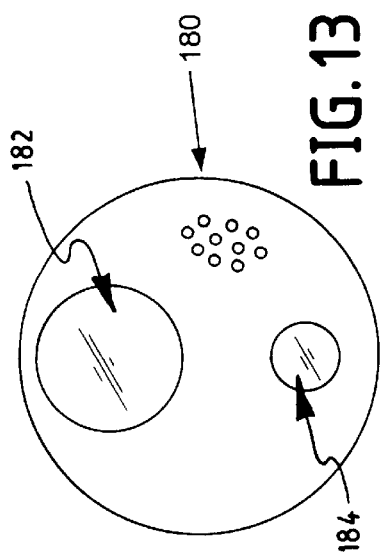
FIG. 13 is a front-elevational view of the endoscope of FIG. 12 looking along the optical axis as indicated by the line A—A.

An alternate version of an IR endoscope suitable for practicing the invention is shown in FIG. 11. This version which is designated generally at 159 consists of a germanium objective lens 160, a relay consisting of germanium lenses 162 and 164, a silicon video coupler lens 166, and a warm stop/adapter 168 designed similar in principle to the one described hereinabove.

The constructional data for IR endoscope 159, which includes aspheric surfaces, is given as follows where the circled numerals in FIG. 11 correspond to surfaces called out in the tabular data below:
GENERAL LENS DATA:
Surfaces: 13
Stop: 6
System Aperture :Entrance Pupil Diameter
Ray aiming: On Pupil shift=0
Gaussian Factor: 0.000000

Figure 12:
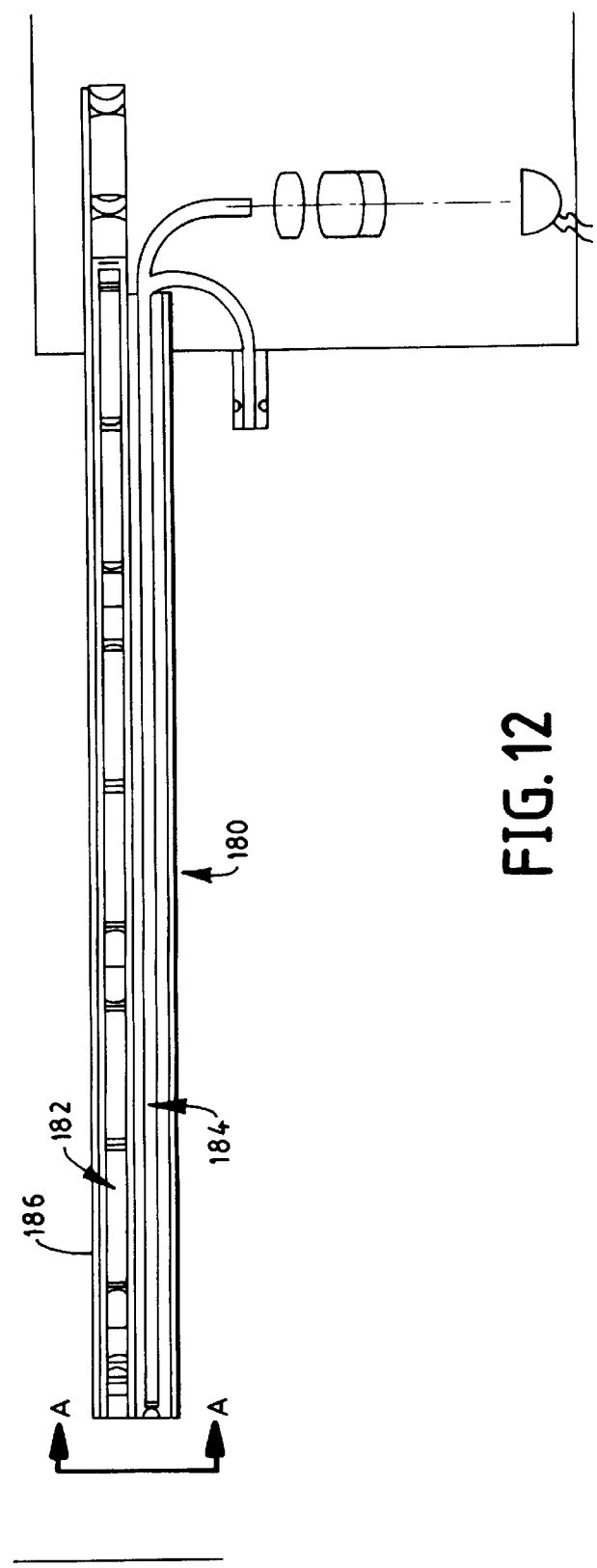
FIG. 12 is another embodiment of the invention in which the infrared and visible endoscopes have been combined for alignment purposes adjacent one another in one tube.

Eff. Focal Len.: 6.61067
Total Track: 144.16
Image Space F/#: 9.72158
Working F/#: 10.787
Obj. Space N.A.: 0.0185359
Stop Radius: −0.35032
Parax. Ima. Hgt.: 5.00554
Parax. Mag.: −0.404643
Entr. Pup. Dia.: 0.68
Entr. Pup. Pos.: −6.66032
Exit Pupil Dia.: 2.24468
Exit Pupil Pos.: −22.7945
Maximum Field: 34
Primary Wave: 4.000000
Lens Units: Millimeters
Angular Mag.: 0.302939
Coeff on r 14: 0
Coeff on r 16: 0
Surface 3: STANDARD
Aperture: Circular Aperture
Minimum Radius: 0
Maximum Radius: 3.6
Surface 4: EVENASPH
Coeff on r 2: −5.8285e-005
Coeff on r 4: 2.2923e-007
Coeff on r 6: −1.5706e-009
Coeff on r 8: 0
Coeffonr 10: 0
Coeff on r 12: 0
Coeff on r 14: 0
Coeff on r 16: 0
Surface 5: STANDARD
Surface STO: STANDARD
Surface 7: STANDARD
Surface 8: EVENASPH
Coeff on r 2: 5.8285e-005
Coeff on r 4: −2.2923e-007
Coeff on r 6: 1.5706e-009
Coeffon r 8: 0
Coeff on r 10: 0
Coeff on r 12: 0
Coeffonr 14: 0
Coeff on r 16: 0
Surface 9: STANDARD
Surface 10: STANDARD
Surface 11: STANDARD
Surface 12: STANDARD
Aperture: Circular Aperture
Minimum Radius: 0
Maximum Radius: 2.2
Surface IMA: STANDARD Reference is now made to FIGS. 12 and which show an embodiment 180 of the invention in which an IR endoscope 182 and a visible endoscope 184 are resident in a common tube 186 such that they are coaxially aligned to provide overlapping views of common fields representing IR images and visible images. The overlapping views would, of course, contain common subject matter that is substantially coextensive. Here, the visible channel may be made substantially smaller in diameter than the IR channel so that the two may still be used with standard sized cannula up to about 15 mm.

Those skilled in the art may make other changes to the invention without departing from the scope of its teachings. Aside from medical applications, it would be possible in appropriate circumstances to use the invention for industrial applications. Moreover, it will also be appreciated by those skilled in the art that the lenses of the invention may be fabricated of ZnSe, ZnSu, Irtran I and II, and CaFl. Therefore, it is intended that the embodiments described herein be considered as illustrative and not be construed in a limiting sense.

What is claimed is:

1. A differential thermal relaxation endodiagnostic method for visually differentiating between normal and abnormal interior body structures, said method comprising:

forming an endoscopic image of infrared radiation emitted within the range including 2 to 14 microns from preselected interior body structures of interest;

detecting said image and generating a video signal thereof where different levels of said infrared radiation are encoded from a preselected gamut of colors;

displaying said encoded video signal so that it can be inspected by an observer; and cooling said preselected interior body structures of interest and then gradually allowing them to return to thermal equilibrium with their surroundings to promote thermal contrast between said preselected interior body structures of interest as they thermally equilibrate at different rates while simultaneously monitoring said endoscopic image and analyzing it for differences in temperature indicative of abnormal interior body structures.

2. The method of claim 1 wherein said step of cooling said preselected interior body structures of interest and then gradually allowing them to return to thermal equilibrium with their surroundings to promote thermal contrast in said infrared image between body structures that thermally equilibrate at different rates comprises flooding said preselected interior body structures with a liquid substantially at room temperature.

3. The method of claim 2 wherein said liquid is selected from the group comprising room temperature saline and Ringer's solution.

4. The method of claim 2 wherein said step of forming said endoscopic image utilizes an IR endoscope comprising a refractive objective lens for forming a real image of said interior body structures of interest in an image plane; at least one relay section consisting solely of refracting elements for transferring said real image to form an intermediate image in a conjugate plane located near the proximal end of system; and a refracting coupling lens for forming a final image of said intermediate image in a detector plane located at the proximal end of said system.

5. The method of claim 2 further including the step of forming another endoscopic image of said preselected body structures of interest in the visible region of the spectrum prior to forming any infrared images and cooling said preselected body structures of interest.

* * * * *